United States Patent [19]

Chang

[11] Patent Number: 5,298,026
[45] Date of Patent: Mar. 29, 1994

[54] METHOD AND APPARATUS FOR LASER MEDICAL TREATMENT

[75] Inventor: Hsuan Chang, Clifton Park, N.Y.

[73] Assignee: General Electric Company, Schenectady, N.Y.

[21] Appl. No.: 917,884

[22] Filed: Jul. 23, 1992

[51] Int. Cl.$^5$ ............................................. A61B 17/36
[52] U.S. Cl. ................................. 606/15; 128/395; 128/898; 606/16
[58] Field of Search .................... 606/15, 16, 17, 7; 128/395, 397, 398; 604/281

[56] References Cited

U.S. PATENT DOCUMENTS

| | | | |
|---|---|---|---|
| 4,461,284 | 7/1984 | Doi | 606/15 |
| 4,850,351 | 7/1989 | Herman et al. | 606/16 |
| 4,862,887 | 9/1989 | Weber et al. | 606/7 |

OTHER PUBLICATIONS

"Lasers in Neurosurgery", Edited by R. V. Jeffreys, Cover page, Copyright page, pp. 48, 49, 288, 289.

*Primary Examiner*—Stephen C. Pellegrino
*Assistant Examiner*—Sonya C. Harris
*Attorney, Agent, or Firm*—Paul R. Webb, II

[57] ABSTRACT

A tumor or other condition within a patient is treated by the application of laser energy through multiple optical fibers, all of which are disposed within a general guiding or outer tube. The optical fibers extend to within the patient by way of a single burr hole. Specifically, each optical fiber is disposed within a corresponding inner tube and each inner tube is disposed within the outer tube and is movable with respect to the outer tube. Each of the inner tubes is flexible and has a permanent bend disposed therein. Each inner tube is placed within the patient by way of the outer tube with the inner tube in a retracted or high energy state. In the retracted or high energy state, each inner tube is bent into a position constrained by the outer tube. Upon the outer tube being positioned at the tumor or other treatment zone, relative movement between the inner tubes and the outer tube frees the inner tubes from being constrained in the high energy or retracted state. The inner tubes then resume their low energy or relaxed state. Since the optical fibers are within the inner tubes, the optical fibers then assume an orientation as determined by the relaxed state of the inner tubes. Laser energy can be supplied through the optical fibers to create a treatment zone much larger than would otherwise be available from a single burr hole.

21 Claims, 2 Drawing Sheets

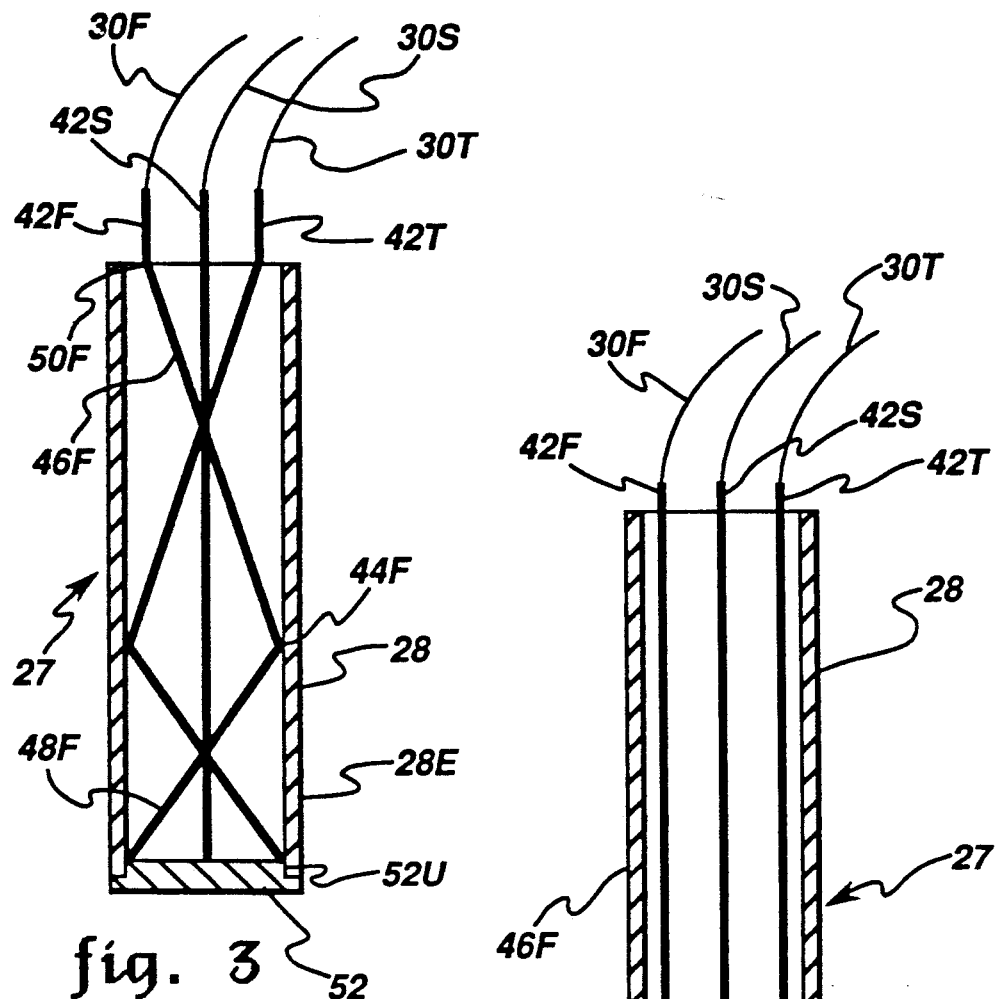
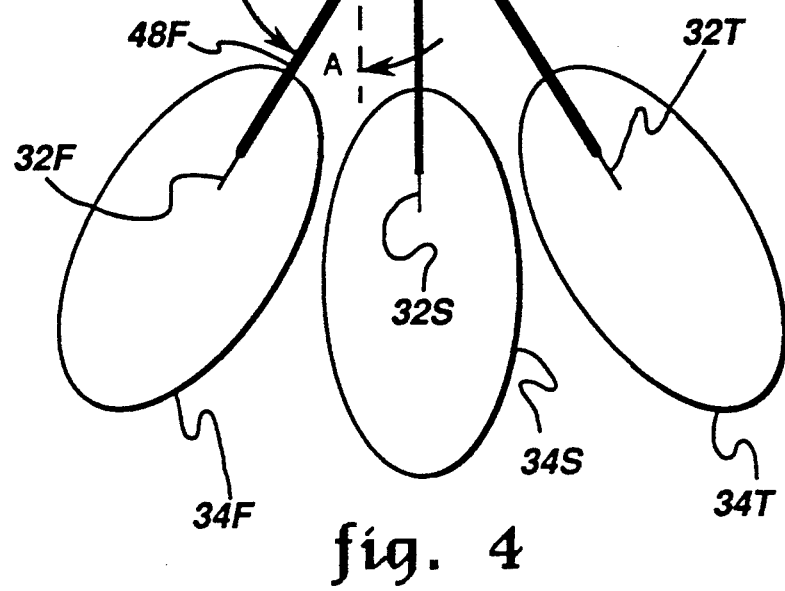

METHOD AND APPARATUS FOR LASER MEDICAL TREATMENT

BACKGROUND OF THE INVENTION

The present invention relates to the treatment of a patient by use of laser energy. More specifically, the present invention relates to treatment of a large volume, such as a large tumor, by use of minimal incisions.

In interstitial laser hyperthermia, a tumor volume is heated to its biological critical temperature to create permanent damage to the tissue so that a lesion is formed in place of the volume. For neurological applications, a burr hole drill is made at the incision point on the skull to allow access of the laser fiber through a guiding tube to the volume of interest. Using a YAG laser, a typically treated volume created under typical laser power controlled by the heat propagation in live tissue is on the order of an ellipsoid with axes of (10, 5, 5) in millimeters. In other words, and assuming the major axis extended in the x direction, the ellipsoid would extend 10 millimeters in the x direction and would have minor axes of 5 millimeters in both the y and z directions. However, in most cases, the tumor volume is larger than the ellipsoid created by a single laser fiber. As shown in the prior art simplified schematic of FIG. 1, an optical fiber 10 extends into the head 12 of a patient by way of a burr hole 14. More specifically, the fiber 10 extends through a guiding tube 16 such that the tip of the fiber 10 is within or immediately adjacent to a tumor volume 18. Laser energy is then supplied through the optical fiber 10 to create an ellipsoid heat/lesion volume 20 of the size previously discussed. As illustrated schematically in FIG. 1, the heat/lesion volume 20 is smaller than the tumor volume 18. Accordingly, lesions would have to be made at different locations in order to cover the tumor volume 18.

In order to create a lesion larger than the typical ellipsoid, multiple laser fibers spaced apart in parallel trajectories have been used to create a heat front that encloses the tumor volume. Alternately, laser energy is applied by multiple fibers spaced apart through different trajectories when access is limited by critical anatomical features such as a blood vessel. Whether one is using spaced apart parallel trajectories or using different nonparallel trajectories, multiple burr holes are often required to allow multiple guiding tubes to access the tumor. (This is true whether the laser energy is applied simultaneously through different fibers or the laser energy is applied in sequence, using one optical fiber at a time.) The requirement for multiple burr holes increases the invasiveness of the operation and makes surgical planning more complicated because multiple trajectories require access through a larger region of anatomy.

OBJECTS AND SUMMARY OF THE INVENTION

Accordingly, it is a primary object of the present invention to provide a new and improved technique for laser treatment of volumes, such as large tumors, through a single incision or at least a minimal number of incisions.

A more specific object of the present invention is to provide for laser medical heating with reduced complexity of treatment.

A still further object of the present invention is to provide for laser treatment with a reduced healing period because it creates a smaller wound than usual.

Yet another object of the present invention is to provide laser hyperthermia treatment having a simplified planning.

The above and other objects of the present invention which will become more apparent as the description proceeds are realized by a medical laser treatment apparatus including an outer tube having a treatment end for disposal at a treatment zone in a patient and a remote end opposite from the treatment end. A plurality of flexible inner tubes are disposed in a high energy retracted state at least partially within the outer tube. Each inner tube has an optical fiber accommodating hole extending lengthwise therein. The high energy retracted state corresponds to each inner tube being constrained to be in a shape other than its free or unconstrained shape. The inner tubes are movable relative to the outer tube to cause each inner tube to assume a non-linear extended position at least partly within the outer tube for application of laser energy using a beam which is not parallel with the outer tube (i.e., parallel with a tangent to the treatment end of a central axis of symmetry of the outer tube if the outer tube is curved lengthwise). The extended position for each inner tube is its free or unconstrained shape. The free or unconstrained shape of each inner tube includes two straight portions connected by a permanent bend. The high energy constrained state of each inner tube includes a temporary bend. The permanent bend of each inner tube is at least partially temporarily straightened when the inner tube is in its high energy restricted state. All of the inner tubes are identically constructed and shaped. There are at least three of the inner tubes. The outer tube has an inner diameter of at least three millimeters. The apparatus further includes a plurality of optical fibers. Each optical fiber is within the optical fiber accommodating hole in a corresponding one of the inner tubes. The outer tube is linear (i.e., is a straight line) and one of the straight portions of each inner tube is parallel thereto when the inner tube is in its extended position. Each of the optical fibers is movable relative to its corresponding inner tube.

The method of laser treatment according to the present invention includes the inserting of a treatment end of an outer tube at a treatment zone in a patient, the outer tube having a remote end opposite to the treatment end. By movement relative to the outer tube, each of a plurality of flexible inner tubes is changed from a high energy retracted state at least partially within the outer tube to a non-linear extended position at least partially within the outer tube. Laser energy is applied to the treatment zone by way of a plurality of optical fibers, each optical fiber disposed in an optical fiber accommodating hole extending lengthwise in a corresponding one of the inner tubes while the inner tube is in its extended position. A beam exits from each optical fiber, which beam is not parallel with the outer tube. The inner tubes are disposed in their high energy retracted states at least partially within the outer tube when the inserting step is performed. Each optical fiber is within its corresponding inner tube when the inserting step is performed. The changing step is performed by holding the inner tubes while pulling back the outer tube. Alternately, the changing step is performed by holding the outer tube while pushing each inner tube (i.e., all inner tubes could be pushed at a time until all of the inner tubes are eventually pushed). The laser energy is applied through all of the optical fibers at the same time. Alternately, the laser energy is applied sequentially through one of the optical fibers at a time. Note that the laser energy may be applied through one optical fiber when its corresponding inner tube is in its extended state even though another inner tube may still remain in its high energy retracted state. The laser energy is used to cause laser hyperthermia of a tumor in the treatment zone.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 3 is a side cross section view of the apparatus of the present invention with inner guiding tubes retracted within an outer of general guiding tube; and FIG. 4 is a side cross section view similar to FIG. 3 except that the inner guiding tubes have been moved into an extended position.

DETAILED DESCRIPTION

Figure 1:
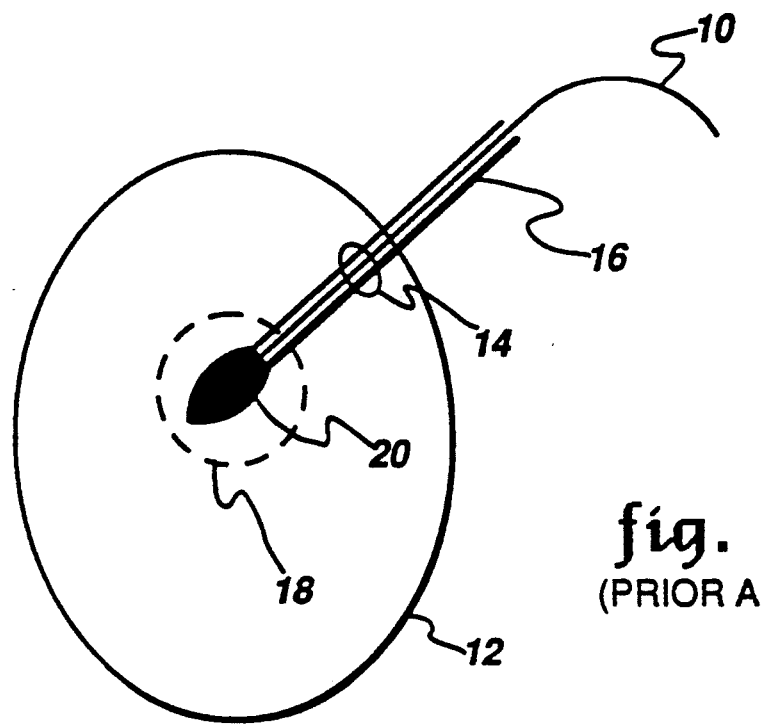
FIG. 1 is a simplified schematic of a prior art laser hyperthermia technique.
Figure 2:
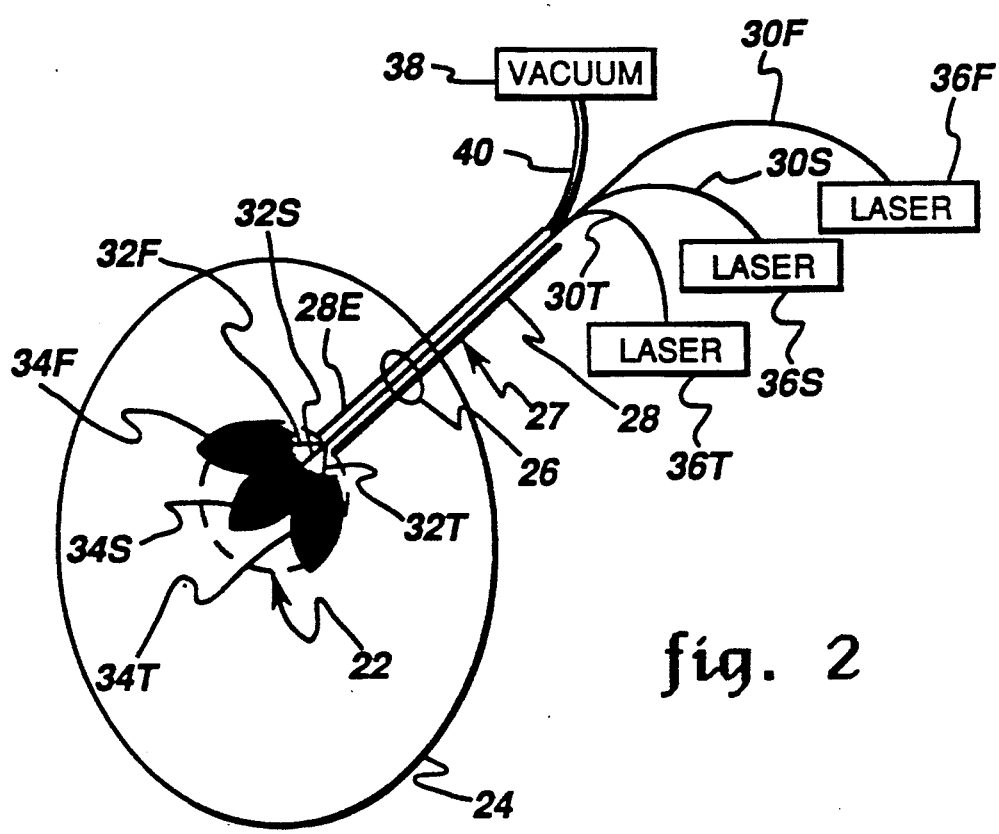
FIG. 2 shows a simplified schematic of the treatment technique of the present invention.

FIG. 2 shows the general concept of the present invention as used to treat a tumor volume 22 within the head 24 of a patient, the tumor volume 22 being accessed by a single burr hole 26 in the skull. Specifically, the apparatus 27 includes an outer guiding tube 28 with first, second, and third optical fibers 30F, 30S, and 30T extending therethrough. The tips 32F, 32S, and 32T of respective optical fibers 30F, 30S, and 30T extend out the tumor-adjacent end 28E of guiding tube 28 so as to respectively create heat/lesion volumes or ellipsoids 34F, 34S, and 34T when corresponding respective first, second, and third lasers 36F, 36S, and 36T are used to apply laser energy to the tumor volume 22. By using a plurality of fibers extending through a single burr hole 26, one can create a combined heat or lesion volume corresponding to the combination of ellipsoids 34F, 34S, and 34T. That combined lesion can be used to treat the relatively large tumor volume 22 without usually requiring additional burr holes. Even if the tumor volume is sufficiently large relative to the pattern of heat created by the various optical fibers such that multiple burr holes would be required, the number of burr holes would be substantially reduced from what would otherwise be required.

As further shown schematically in FIG. 2, a vacuum 38 may be connected to the upper end of guiding tube 28 by way of a tube 40 so as to suction out gases which may be produced by the application of laser energy within the tumor volume 22. Although not shown, an interface adaptor may be used to connect the suction tube 40 to the upper end of guide tube 28. The interface may simply be a cover which closes off the upper end of guiding tube 28, the cover having one or more exit holes for the optical fibers 30F, 30S, and 30T and having a hole corresponding to the suction tube 40. When the vacuum 38 is turned on, the inside of guide tube 28 is suctioned so that gas produced from the application of laser energy to the tumor volume 22 would be drawn through the guide tube 28 into the suction tube 40 and into the vacuum 38. In order for the guide tube 28 to work properly with the optional vacuum 38, the guide tube 28 must be of sufficient diameter so as to accommodate the various optical fibers, while allowing passage of gas therein.

Although FIG. 2 illustrates a separate laser for each of the optical fibers 30F, 30S and 30T, a single such laser could be used. The single laser could supply laser energy to one of the optical fibers at a time or could, by use of beam splitters (not shown) or other optical devices, supply laser energy to all of the optical fibers at the same time.

Turning now to FIG. 3, the manner in which the optical fibers 30F, 30S, and 30T extend through the outer guide tube 28 of apparatus 27 will be discussed. Flexible guiding tubes 42F, 42S, and 42T respectively hold optical fibers 30F, 30S, and 30T. Each of the flexible or inner tubes 42F, 42S, and 42T is disposed within the outer or general guiding tube 28, which is rigid and made of surgical stainless steel using known techniques. The flexible or inner tubes 42F, 42S, and 42T may also be made of surgical stainless steel. Considering FIG. 4 in conjunction with FIG. 3, each of the flexible or inner tubes 42F, 42S, and 42T would be identically constructed to have a permanent bend such as 44F disposed therein. (The bend in tube 44S is not visible from the plane of view of FIGS. 3 and 4.) As shown in FIG. 4, the inner tube 42F is in a relaxed state and extended position wherein it has an upper straight section 46F separated from a lower straight section 48F by the permanent bend 44F. The inner tubes 42S and 42T are made the same way as inner tube 42F. Although the inner tube 42F would normally assume the position of FIG. 4, inner tube 42F is made of a flexible surgical stainless steel so that it can be forced into a retracted position shown in FIG. 3. In the high energy state or retracted position of FIG. 3, the inner tube 42F has a bend 50F disposed therein. This temporary bend 50F may be closer to the permanent bend 44F or further from it depending upon the relationship of the diameters and lengths of tubes 42F and 28. Also, the permanent bend 44F is temporarily at least partially straightened when the inner tube 42F is retreated. In the view of FIG. 3, the inner tubes 42S and 42T would likewise be in a high energy state or retracted position.

When one wishes to treat a tumor using the technique of FIG. 2, one would start with the assembly of FIG. 3. The burr hole 26 (FIG. 2 only) is placed in the appropriate part of the patient's skull. The general guide tube 28 is inserted into the patient until its lower end 28E is at (i.e., inside or adjacent to) the volume which is to be treated. When the guide tube 28 is inserted, the flexible inner tubes 42F, 42S, and 42T are already disposed in their high energy state within the general guide tube 28 and as shown in FIG. 3. An optional cover 52 (FIG. 3 only) may be used to minimize the risk of materials entering the guide tube 28 while it is inserted into the patient to the location of the tumor or other volume to be treated. The cover 52 may be secured to the outside of guide tube 28 by an upwardly extending portion 52U which extends circumferentially around the inner wall of the cylindrical guide tube 28. If desired, clamps (not shown) could be used to hold the upper ends of the flexible inner tubes 42F, 42S, and 42T to the upper end of guide tube 28 when the guide tube 28 is being moved.

Upon the general guide tube 28 being placed adjacent to the volume which is to be treated, it is necessary to allow the flexible inner tubes 42F, 42S, and 42T to assume their extended positions. The optional clamps (not shown) which secure them to the upper end of guide tube 28 would be removed if such clamps were used.

A first technique for extending the flexible tubes is to simply have the surgeon or other medical person push each of the flexible tubes 42F, 42S, and 42T down. The thin plastic or other easily punctured material of the optional cover 52, if any, would be punctured and pushed aside as the flexible tubes 42F, 42S, and 42T move from their FIG. 3 position into their FIG. 4 positions. Specifically, the bend 44F of tube 42F, as well as the similar permanent bends in tubes 42S and 42T, would move clear of the guide tube 28. Each of the flexible tubes 42F, 42S, and 42T would assume its relaxed state in an extended position and the temporary bends, such as bend 50F in tube 42F shown in FIG. 3, would be straightened out. Thus, each of the inner tubes 42F, 42S, and 42T is a spring which assumes its relaxed state (free or unconstrained shape) of FIG. 4 when not constrained (FIG. 4). When constrained by having permanent bends such as 44F disposed within the outer tube 28, the FIG. 3 position or state is assumed. It should again be emphasized that tube 42S is the same in structure as tube 42F and the bends (one permanent, one temporary) in tube 42S are simply not visible because the bends of that tube would be in the plane of view used for FIGS. 3 and 4.

An alternate technique for positioning the inner tubes 42F, 42S, and 42T relative to the outer or general guide tube 28 would involve the physician holding the upper ends of each of the flexible tubes 42F, 42S, and 42T stationary and, at the same time, pulling the general guide tube 28 out away from the tumor or other volume to be treated. Under this procedure, any optional cover such as cover 52 would be punctured and folded aside as the flexible tubes 42F, 42S, and 42T assume the position shown in FIG. 4. The guide tube 28 would be pulled back sufficiently far that the permanent bends, such as bend 44F in flexible tube 42F, would be free of outer or guide tube 28.

The medical personnel use x-ray or CT images in known fashion to position the various tubes relative to the tumor.

Whether one pushes the flexible tubes relative to the outer tube or pulls the outer tube relative to the flexible tubes may depend on the type of tissue for which treatment is desired. For example, if treating brain tissue, retracting the outer tube 28 may minimize the risk that the flexible tubes would damage healthy tissue when assuming their relaxed states shown in FIG. 4. In the case of brain tissue, it may be advantageous to initially puncture the tumor by using the lower end 28E of guide or outer tube 28. Then upon pulling back on the guide tube 28, the flexible tubes would be expanding within the tumor and would be less likely to damage adjacent healthy tissue. Additionally, pulling back on the general guide tube 28 may allow one to position the apparatus in a simpler fashion. That is, pulling back of the outer tube 28 may be simpler in practice than pushing forward with each of the three or more flexible tubes. However, there are advantages in certain situations to pushing the flexible tubes 42F, 42S, and 42T relative to the general or outer tube 28. For example, if operating in muscle tissue, such as in the abdomen, the flexible tubes 42F, 42S, and 42T may be able to push aside muscle tissue, without damaging it, whereas the same muscle tissue might have been damaged by contact with the general or outer guiding tube 28. Further, there may be some advantages in particular situations of pushing out one of the flexible or inner tubes at a time, applying laser energy through an optical fiber within the flexible tube, and then pushing out the next flexible tube.

Once the flexible tubes 42F, 42S, and 42T have been moved from their FIG. 3 high energy states to their FIG. 4 relaxed states, one may push downwardly on each of the optical fibers 30F, 30S, and 30T such that each of the optical fibers has a small tip portion respectively, 32F, 32S, and 32T which extends out of the corresponding flexible tube. If desired, indicia (not shown) may be applied to the optical fibers so as to indicate how far the optical fibers should be pushed relative to the upper ends of the corresponding flexible tubes. Instead of pushing out the optical fibers from the flexible tubes, the optical fibers may have originally been positioned with very small portions extending out of the flexible tubes. Although that avoids the need for any movement of the optical fibers 30F, 30S, and 30T relative to their corresponding flexible tubes 42F, 42S, and 42T, this may somewhat increase the chance that the optical fiber's tip would be damaged when the corresponding flexible tube is moved relative to the general guiding or outer tube 28.

Once the apparatus 27 has assumed the position of FIG. 4, one may apply laser energy through each of the optical fibers 30F, 30S, and 30T in order to create the heat/lesion volumes 34F, 34S, and 34T shown in FIGS. 2 and 4. If desired, one may supply laser energy (lasers shown in FIG. 2 only) through only a single one of the optical fibers at a time. Alternately, one may provide laser energy through all of the optical fibers at the same time. Providing laser energy through all of the optical fibers at the same time may provide a more even temperature distribution, but may slightly increase the chances that the temperature would be so high as to cause charring or other undesirable effects. The medical personnel may subject the patent to ultrasound imaging during the procedure so as to monitor temperature and minimize the risk of problems. If the temperature gets too high, gases may form and make it hard to control the temperature distribution. To reduce the risk of uncontrolled temperature distribution from the formation of gas bubbles, a vacuum 38 (FIG. 2 only) may be used in the manner discussed above. The vacuum should create only a relatively low suction at the tip 28E of the outer tube 28 so as to minimize the possibility of accidentally damaging tissue from a strong suction or vacuum. As mentioned previously, the vacuum 38 may operate by way of a suction tube 40 interfaced through a cover (not shown) to the upper end of the general guiding tube 28. However, considering that only a relatively low suction or vacuum needs to be created, such a cover may not be necessary depending upon the power of the vacuum 38.

The general guiding or outer tube 28 would preferably have an inside diameter of 3 to 5 millimeters and an outside diameter of 5 to 7 millimeters if used for brain surgery. If the general guiding or outer tube 28 is to be used for surgery other than brain surgery (such as abdominal surgery), larger outside diameters may be used. Depending upon the relative sizes of the flexible or inner guiding tubes 42F, 42S, and 42T, and the general guiding or outer tube 28, more than 3 of the flexible tubes might be used. Specifically, the use of a larger number of flexible tubes will improve the uniformity of the temperature distribution and will allow one to treat a larger volume. However, use of too many tubes would increase the chances of the inner tubes becoming entangled with each other and/or would require one to use a larger outer tube. (It is preferable to use a smaller outer tube so that the burr hole may be smaller.) The outer tube 28 may be made of surgical stainless steel and would be relatively rigid.

The flexible or inner guiding tubes 42F, 42S, and 42T would be made of surgical stainless steel and would have permanent bends, such as 44F, placed therein using known techniques. The flexible tubes would have an outside diameter of just over one millimeter and would have an inside diameter just greater than the amount needed to accommodate an optical fiber. Since the optical fiber would generally have a diameter of between 400 and 600 microns, the inside diameter of the flexible tube should be just larger than that.

The ellipsoidal patterns generated by the laser energy from optical fibers 30F, 30S, and 30T correspond to bare tips of the optical fibers. In other words, the temperature distributions shown by the ellipsoidal patterns of FIGS. 2 and 4 have assumed that the optical fibers have no special structures at their tips. One could alternately use various known structures at the tips of the optical fibers to change the distribution of laser energy and the resulting temperature distribution. Further, one might alternately use optical fibers which supply energy through a window (not shown) in an inner tube. Various arrangements have been developed to allow laser energy to be passed from an optical fiber to the tissue of a patient, while minimizing the contact between the patient's tissues and the actual optical fiber. If desired, such structures could be used in combination with the present invention.

The structure of FIG. 3 could be made as a disposable unit with the inner tubes 42F, 42S, and 42T clamped (clamps not shown) to the upper end of the general guiding or outer tube 28. Whether the apparatus of FIG. 3 is made as a disposable unit or as a reusable unit, one might make different versions having different patterns of temperature distribution. With reference to FIG. 4, the angle corresponding to bend 44F is angle A. Devices could, for example, be made where the angle A is 20° to provide a particular temperature distribution, where the angle A is 30° to provide a second temperature distribution pattern, and where the angle A is 40° to provide a third temperature distribution pattern.

Although the present invention is designed to minimize the need for multiple burr holes, it may still be necessary to use more than one burr hole if a particular tumor or other treatment zone has such a large volume that the front created by the laser energy from the optical fibers would be too small for adequate treatment. Even though multiple burr holes might then be required for use of the present invention, the number of burr holes would still be significantly less than would otherwise be required.

In addition to providing the surgeon with the option of applying laser energy through all of the optical fibers at the same time or sequentially through different combinations of the fibers, the surgeon could use different amounts of laser power through different ones of the optical fibers in order to provide a desired temperature distribution.

Although specific constructions and arrangements have been discussed herein, it is to be understood that these are for illustrative purposes only. Various modifications and adaptations will be apparent to those of skill in the art. Accordingly, the scope of the present invention should be determined by reference to the claims appended hereto.

What is claimed is:

1. A medical treatment apparatus comprising an outer tube having a treatment end for disposal at a treatment zone in a patient and remote end opposite to the treatment end, and a plurality of flexible inner tubes disposed in a high energy retracted state at least partially within said outer tube, each inner tube having an optical fiber accommodating hole extending lengthwise therein, each inner tube being non-linear when unconstrained, the high energy retracted state corresponding to each inner tube being constrained by said outer tube, the high energy retracted state of each inner tube corresponding to each inner tube having a shape different from its shape when unconstrained, and wherein said inner tubes are movable relative to said outer tube to cause each inner tube to assume a non-linear extended position at least partly within said outer tube for application of laser energy using a beam which is not parallel with the outer tube, and further comprising a plurality of optical fibers, each optical fiber corresponding to one of said inner tubes and disposed within the optical fiber accommodating hole of said corresponding one of said inner tubes.

2. The medical treatment apparatus of claim 1 wherein the extended position for each inner tube corresponds to that inner tube being unconstrained.

3. The medical treatment apparatus of claim 2 wherein each inner tube includes two straight portions connected by a permanent bend when unconstrained.

4. The medical treatment apparatus of claim 3 wherein the high energy retracted state of each inner tube includes a temporary bend.

5. The medical treatment apparatus of claim 4 wherein the permanent bend of each inner tube is at least partially, temporarily straightened when the inner tube is in its high energy retracted state.

6. The medical treatment apparatus of claim 5 wherein all of said inner tubes are identically constructed and shaped.

7. The medical treatment apparatus of claim 5 wherein there are at least three of said inner tubes.

8. The medical treatment apparatus of claim 1 wherein each inner tube consists of two straight portions connected by a permanent bend when unconstrained.

9. The medical treatment apparatus of claim 1 wherein said outer tube has an inner diameter of at least 3 mm.

10. The medical treatment apparatus of claim 1 wherein each inner tube includes two straight portions connected by a permanent bend when unconstrained.

11. The medical treatment apparatus of claim 10 wherein said outer tube is linear and one of the straight portions of each inner tube is parallel thereto when that inner tube is in its extended position.

12. The medical treatment apparatus of claim 11 wherein there are at least three of said inner tubes, wherein said outer tube has an inner diameter of at least 3 mm, and wherein each of said optical fibers is movable relative to its corresponding inner tube.

13. A method of laser treatment comprising the steps of:

inserting the treatment end of an outer tube at a treatment zone in a patient, said outer tube having a remote end opposite to the treatment end;

changing each of a plurality of flexible inner tubes from a high energy retracted state at least partially within the outer tube to a non-linear extended position at least partially within said outer tube, said changing step performed by moving said outer tube relative to said inner tubes; and applying laser energy to the treatment zone by way of a plurality of optical fibers, each optical fiber extending in an optical fiber accommodating hole extending lengthwise in a corresponding one of the inner tubes and having a beam exiting from it which is not parallel with the outer tube.

14. The method of laser treatment of claim 13 wherein the inner tubes are disposed in their high energy retracted states at least partially within the outer tube when the inserting step is performed.

15. The method of laser treatment of claim 14 wherein each optical fiber is within its corresponding inner tube when the inserting step is performed.

16. The method of laser treatment of claim 15 wherein each inner tube is unconstrained when in its extended position, wherein each inner tube includes two straight portions connected by a permanent bend when unconstrained, wherein the high energy retracted state of each inner tube includes a temporary bend, and wherein there are at least three of said inner tubes.

17. The method of laser treatment of claim 14 wherein the changing step is performed by holding the inner tubes while pulling back the outer tube.

18. The method of laser treatment of claim 14 wherein the changing step is performed by holding the outer tube while pushing each inner tube.

19. The method of laser treatment of claim 14 wherein laser energy is applied through all of the optical fibers at the same time.

20. The method of laser treatment of claim 14 wherein laser energy is applied sequentially through one of the optical fibers at a time.

21. The method of laser treatment of claim 13 wherein the laser energy causes laser hyperthermia of a tumor in said treatment zone.

* * * * *